US011112272B2

(12) United States Patent
Nagao (10) Patent No.: US 11,112,272 B2
(45) Date of Patent: Sep. 7, 2021

(54) SENSOR INFORMATION MANAGEMENT SYSTEMS AND METHODS

(71) Applicant: Intertrust Technologies Corporation, Sunnyvale, CA (US)

(72) Inventor: Yutaka Nagao, Cupertino, CA (US)

(73) Assignee: Intertrust Technologies Corporation, Sunnyvale, CA (US)

(*) Notice: Subject to any disclaimer, the term of this patent is extended or adjusted under 35 U.S.C. 154(b) by 0 days.

(21) Appl. No.: 16/396,900

(22) Filed: Apr. 29, 2019

(65) Prior Publication Data

US 2020/0088545 A1 Mar. 19, 2020

Related U.S. Application Data

(63) Continuation of application No. 14/884,629, filed on Oct. 15, 2015, now Pat. No. 10,317,243.

(51) Int. Cl.
| | |
|---|---|
| *G01C 21/20* | (2006.01) |
| *G01D 1/10* | (2006.01) |
| *G01D 21/00* | (2006.01) |
| *G01D 3/08* | (2006.01) |
| *G01W 1/02* | (2006.01) |
| *G01N 33/00* | (2006.01) |

(Continued)

(52) U.S. Cl.
CPC .............. *G01D 3/08* (2013.01); *G01C 21/20* (2013.01); *G01D 1/10* (2013.01); *G01D 21/00* (2013.01); *G01N 33/0075* (2013.01); *G01W 1/02* (2013.01); *G01C 21/34* (2013.01); *G06Q 50/30* (2013.01)

(58) Field of Classification Search
CPC ...... G01C 21/165; G01C 21/20; G01C 21/34; G06F 13/00; G01D 1/10; G01D 21/00; G01D 3/08; G01N 33/0075; G01W 1/02; G06Q 50/30
USPC ....... 340/2.1, 3.1, 439, 576, 988; 455/456.1, 455/456.3; 701/29.6, 33.2; 702/1–3, 702/127, 142, 150, 187–189
See application file for complete search history.

(56) References Cited

U.S. PATENT DOCUMENTS

| | | |
|---|---|---|
| 8,234,387 B2 | 7/2012 | Bradley et al. |
| 8,776,216 B2 | 7/2014 | Boccon-Gibod et al. |

(Continued)

FOREIGN PATENT DOCUMENTS

| | | |
|---|---|---|
| CN | 101043407 A | 9/2007 |
| CN | 102934467 A | 2/2013 |

(Continued)

*Primary Examiner* — Jeffrey P Aiello
(74) *Attorney, Agent, or Firm* — Finnegan, Henderson, Farabow, Garrett & Dunner, LLP (57) ABSTRACT

This disclosure relates to systems and methods for management of information, including environmental information, obtained by a variety of sensors associated with one or more distributed mobile sensor platforms. In certain embodiments, the geographically transitory nature of a mobile sensor platform may be leveraged to facilitate collection of environmental information over a larger geographic area than that of a fixed sensor platform. Embodiments disclosed herein provide for information consistency and/or quality checking of information obtained by mobile sensor platforms. Further embodiments may be used to incentivize the collection and/or acquisition of certain data via point and/or credit based compensation.

13 Claims, 5 Drawing Sheets

(51) Int. Cl.
  *G06Q 50/30* (2012.01)
  *G01C 21/34* (2006.01)

(56) References Cited

U.S. PATENT DOCUMENTS

| | | | |
|---|---|---|---|
| 9,805,601 B1* | 10/2017 | Fields | G08G 1/096791 |
| 2006/0217881 A1* | 9/2006 | Pei | G09B 29/10 |
| | | | 701/432 |
| 2007/0208493 A1 | 9/2007 | Downs et al. | |
| 2008/0207183 A1* | 8/2008 | Root | H04L 67/306 |
| | | | 455/414.2 |
| 2010/0293049 A1 | 11/2010 | Maher et al. | |
| 2013/0096943 A1 | 4/2013 | Carey et al. | |
| 2016/0086285 A1* | 3/2016 | Jordan Peters | G06Q 40/08 |
| | | | 705/4 |
| 2016/0171521 A1* | 6/2016 | Ramirez | G06Q 30/0224 |
| | | | 701/409 |
| 2017/0069208 A1* | 3/2017 | Nair | G01C 21/3415 |

FOREIGN PATENT DOCUMENTS

| | | |
|---|---|---|
| CN | 104270773 A | 1/2015 |
| CN | 104736964 A | 6/2015 |
| EP | 2725532 A1 | 4/2014 |

\* cited by examiner

SENSOR INFORMATION MANAGEMENT SYSTEMS AND METHODS

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

TECHNICAL FIELD

The present disclosure relates generally to systems and methods for managing data obtained by a variety of sensors. More specifically, but not exclusively, the present disclosure relates to systems and methods for managing data obtained by environmental sensors associated with one or more distributed mobile sensor platforms.

BACKGROUND

Information obtained by distributed sensors may be used in a variety of applications. For example, environmental information collected by distributed sensors may be used in connection with certain environmental forecasting activities including, without limitation, weather forecasting, air quality forecasting, allergen forecasting, and/or the like. Environmental information may be further used in connection with a variety of other research endeavors including, for example, environmental modeling, health planning and policy development activities, physical science research, and/or the like.

While information obtained by distributed sensors may be valuable, the deployment and continued maintenance of a network of distributed sensors may be relatively cumbersome and/or expensive, as a large number of sensors may be required to provide sufficient information coverage for a given geographic area. Moreover, individual distributed sensors may be geographically fixed, thereby limiting the utility information collected by such sensors to a particular geographic area.

SUMMARY

Systems and methods disclosed herein facilitate management of data obtained by a variety of sensors associated with one or more distributed mobile sensor platforms. Sensors associated with various sensor platforms, including mobile sensor platforms, may be configured to measure a variety of information including environmental information. For example, sensors may be configured to measure and/or otherwise collect information relating to pollen levels, air particulate levels (e.g., PM 2.5 or the like), wind speed and/or direction, temperature, humidity, noise levels, brightness, ozone levels, and/or any other type of environmental information. Such environmental information may be used in connection with a wide variety of forecasting, modeling, planning, and/or research activities. Although certain embodiments disclosed herein are discussed in connection with environmental information, it will be appreciated that embodiments of the disclosed systems and methods may be used in connection with any other type of data and/or information.

A mobile sensor platform consistent with embodiments of the disclosed systems and methods may comprise any mobile and/or otherwise portable platform, entity, and/or device that may include and/or otherwise be associated with one or more sensors for collecting information that may include environmental information. A mobile sensor platform may include, without limitation, a passenger vehicle, a transit vehicle (e.g., a bus or the like), a train and/or train car, a bicycle, a wearable and/or otherwise portable technology device (e.g., a smartphone or the like), and/or any other type of transportation platform, entity, and/or device that may include and/or otherwise be associated with one or more sensors that may collect data. In further embodiments, the disclosed systems and methods may be used in connection with one or more fixed sensor platforms in addition to and/or in lieu of one or more distributed mobile sensor platforms.

In certain embodiments, the geographically transitory nature of a mobile sensor platform may be leveraged to facilitate collection of environmental information over a larger geographic area than that of a fixed sensor platform. For example, an environmental sensor mounted to a transit vehicle may continuously and/or periodically measure certain environmental information as the transit vehicle traverses a transit route. Measured environmental information may be communicated from the environmental sensor and/or the transit vehicle to one or more environmental information service provider systems (e.g., communicated continuously, periodically, upon establishing communication, and/or the like). By collecting environmental information as the transit vehicle traverses a transit route, information associated with a number of geographic locations and/or over a wider geographic area may be obtained.

Consistent with certain embodiments disclosed herein, information consistency and/or quality checking may be performed by an information service provider system configured to aggregate information collected by a plurality of sensors. For example, an environmental information service provider system may compare a plurality of environmental information data points obtained by sensors of a plurality of mobile sensor platforms at a same and/or similar geographic location and/or time to identify outlier data points. In some embodiments, the environmental information service provider system may be further configured to score and/or otherwise attribute certain weights data points based on such a consistency and/or quality checking determination. For example, data points having relatively high consistency and/or correlation with other similar data points (e.g., proximately and/or temporally similar data points) may be attributed, with a higher score and/or weight, whereas outlier data points may be attributed, with a lower score and/or weight.

Systems and methods disclosed herein may further be used to incentivize the collection and/or acquisition of certain information. For example, in some embodiments, an environmental information service provider may identify certain geographic areas, information collection times, and/or information types of interest. Such areas, times, and/or information types of interest may include information that has not been previously collected by one or more mobile sensor platforms, information that has not been collected within a certain time period, and/or information or information that has been collected by a mobile sensor level attributed with less than a threshold score and/or weight. In some embodiments, the environmental service provider may incentivize one or more mobile sensor platforms to obtain such information of interest (e.g., by presenting the mobile sensor platform with an alternative route to a destination and/or travel time). In this manner, the environmental service provider system may increase an amount of relevant environmental data it obtains and/or the coverage (e.g., geographical coverage, temporal coverage, and/or information type coverage) of such data.

BRIEF DESCRIPTION OF THE DRAWINGS

The inventive body of work will be readily understood by referring to the following detailed description in conjunction with the accompanying drawings, in which.

DETAILED DESCRIPTION

A detailed description of the systems and methods consistent with embodiments of the present disclosure is provided below. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The embodiments of the disclosure may be understood by reference to the drawings, wherein like parts may be designated by like numerals. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of any method disclosed herein do not necessarily need to be executed in any specific order, or even sequentially, nor need the steps be executed only once, unless otherwise specified.

Systems and methods are presented facilitating management of data obtained by a variety of sensors associated with one or more distributed mobile sensor platforms. In certain embodiments, the systems and methods described herein can, for example, be used in connection with digital rights management ("DRM") technologies such as those described in commonly assigned, co-pending U.S. patent application Ser. No. 11/583,693 ("the '693 application"), service orchestration technologies such as those described in commonly assigned co-pending U.S. patent application Ser. No. 10/863,551 ("the '551 application"), information storage and/or management technologies such as those described in commonly assigned co-pending U.S. patent application Ser. No. 13/654,349 ("the '349 application"), and/or content delivery technologies such as those described in commonly assigned co-pending U.S. patent application Ser. No. 12/785,406 ("the '406 application") (the contents of the '693 application, the '551 application, the '349 application, and the '406 application hereby being incorporated by reference in their entireties), as well as in other contexts. It will be appreciated that these systems and methods are novel, as are many of the components, systems, and methods employed therein.

Figure 1:
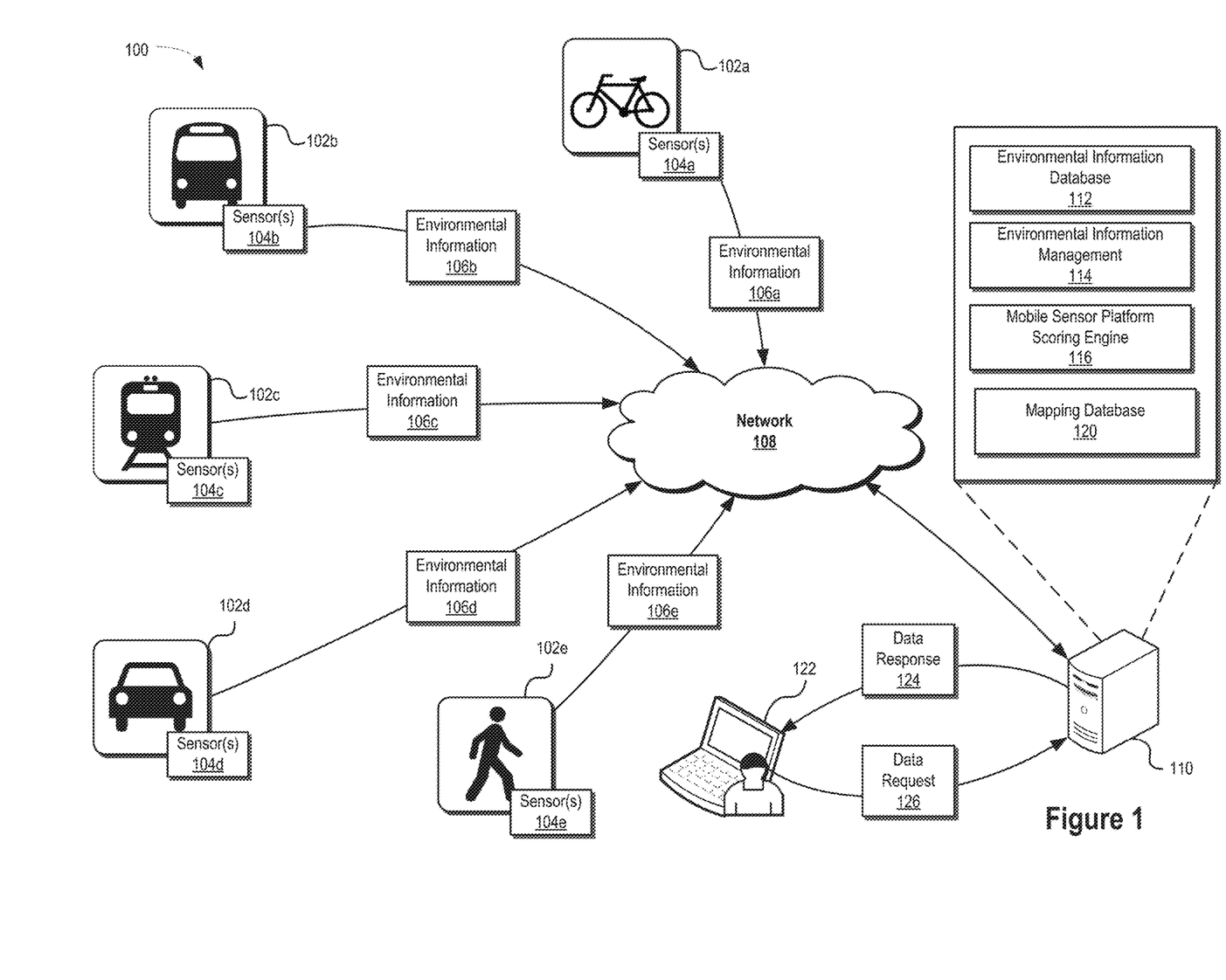
FIG. 1 illustrates an exemplary architecture of an information server provider platform consistent with embodiments of the present disclosure.

FIG. 1 illustrates an exemplary architecture 100 of an information service provider platform consistent with embodiments of the present disclosure. The platform may include an information service provider system 110 configured to implement an information service (e.g., an environmental information service) and a user system 122 configured to, among other things, interact with information managed by the service provider system 110 consistent with embodiments disclosed herein. Although illustrated as separate systems, in certain embodiments, the information service provider system 110 and/or the user system 122 may comprise a single computing system. In further embodiments, the information service provider system 110 and/or the user system 122 may comprise any suitable number and/or combination of computing systems.

The information service provider system 110 may be configured to aggregate, manage, and/or otherwise operate on information 106a-106e collected by one or more distributed mobile sensor platforms 102a-102e and/or associated sensors 104a-104e. In certain embodiments, a user system 122 may be configured to interact with the information service provider system 110 in connection with performing a variety of operations. For example, among other things, the user system 122 may issue requests 126 and/or receive associated responses 124 for information managed by the service provider system 110, for data products derived from the information, for the results of certain computations performed on the information, and/or the like.

Consistent with embodiments disclosed herein, mobile sensor platforms 102a-102e may comprise any mobile and/or or otherwise portable platform, entity, and/or device that may include and/or otherwise be associated with one or more sensors 104a-104e for collecting information. For example, a mobile sensor platform may include, without limitation, a passenger vehicle 102d, a transit vehicle (e.g., a bus 102b or the like), a train 102c and/or train car, a bicycle 102a, a wearable and/or otherwise portable technology device (e.g., a smartphone, a smartwatch, or the like), an individual 102e, and/or any other type of transportation platform, entity, and/or device that may include and/or otherwise be associated with one or more sensors 104a-104e. In further embodiments, the disclosed systems and methods may be used in connection with one or more fixed sensor platforms in addition to and/or in lieu of one or more distributed mobile sensor platforms 102a-102e. In some embodiments, a mobile sensor platform 102a-102e may be spatially transitory in nature, thereby facilitating collection of information over a larger geographic area than that of a fixed sensor platform.

Sensors 104a-104e associated with the various mobile sensor platforms 102a-102e may be configured to measure a variety of information including, for example, environmental information. In certain embodiments, one or more of sensors 104a-104e may be configured to measure and/or otherwise collect a single type of information. In other embodiments, one or more of sensors 104a-104e may be figured to measure and/or otherwise collect a plurality of information types.

In certain embodiments, one or more of sensors 104a-104e may be configured to measure and/or otherwise collect environmental information 106a-106e including, without limitation, information relating to pollen levels, air particulate levels (e.g., PM 2.5 or the like), wind speed and/or direction, temperature, humidity, noise levels, brightness, ozone levels, and/or any other type of environmental information. The one or more sensors 104a-104e may comprise, for example, humidity sensor, temperature sensor, airspeed sensor, rainfall amount sensor, ultraviolet sensor, ozone sensor, atmosphere pressure (or altitude) sensor, particle sensor, aerosol sensor, pollen sensor, PM sensor, odor sensor, CO2 sensor, noise sensor, illumination level sensor, acceleration sensor, gyro sensor, and inclination sensor. Although certain embodiments disclosed herein are discussed in connection with sensors 104a-104e configured to measure and/or otherwise collect environmental information, it will be appreciated that embodiments of the disclosed systems and methods may be used in connection with any other type of sensor and/or data and/or information.

In certain embodiments, one or more of sensors 104a-104e may further comprise a location determination sensor, such as Global Positioning System ("GPS") sensors, although other location determination sensors are also contemplated. In some embodiments, location information obtained by a location determination sensor may be associated with measured and/or collected environmental information 106a-106e. In further embodiments, temporal information may be associated with the measured and/or collected environmental information 106a-106e. Associated measured and/or collected environmental 106a-106e and/or other information, location information, and/or temporal information may be collectively referred to as spatio-temporal information, and may be used in connection with embodiments of the disclosed systems and methods.

The systems 110, 122, mobile sensor platforms 102a-102e, and/or associated sensors 104a-104e may be communicatively coupled via one or more networks 108 comprising one or more connections. The network connections may comprise a variety of network communication devices and/or channels and may utilize any suitable communications protocols and/or standards facilitating communication between the connected devices and systems. The network connections may comprise the Internet, a local area network, a virtual private network, and/or any other communication network utilizing one or more electronic communication technologies and/or standards (e.g., Ethernet or the like). In some embodiments, the network connections may comprise a wireless carrier system such as a personal communications system ("PCS"), and/or any other suitable communication system incorporating any suitable communication standards and/or protocols. In further embodiments, the network connections may comprise an analog mobile communications network and/or a digital mobile communications network utilizing, for example, code division multiple access ("CDMA"), Global System for Mobile Communications or Groupe Special Mobile ("GSM"), frequency division multiple access ("FDMA"), and/or time divisional multiple access ("TDMA") standards. In certain embodiments, the network connections may incorporate one or more satellite communication links. In yet further embodiments, the network connections may utilize IEEE's 802.11 standards, Bluetooth®, ultra-wide band ("UWB"), Zigbee®, and or any other suitable standard or standards.

The systems 110, 122, mobile sensor platforms 102a-102e, and/or associated sensors 104a-104e may comprise any suitable computing system or systems configured to implement embodiments of the systems and methods disclosed herein. In certain embodiments, the systems 110, 122, mobile sensor platforms 102a-102e, and/or associated sensors 104a-104e may comprise at least one processor system configured to execute instructions stored on an associated non-transitory computer-readable storage medium. As discussed in more detail below, the systems 110, 122, mobile sensor platforms 102a-102e, and/or associated sensors 104a-104e may further comprise a secure processing unit ("SPU") configured to perform sensitive operations such as trusted credential and/or key management, secure policy management, and/or other aspects of the systems and methods disclosed herein. The systems 110, 122, mobile sensor platforms 102a-102e, and/or associated sensors 104a-104e may further comprise software and/or hardware configured to enable electronic communication of information between the systems 110, 122, mobile sensor platforms 102a-102e, and/or associated sensors 104a-104e via one or more associated network connections.

Environmental information 106a-106e measured and/or otherwise collected by sensors 104a-104e associated with mobile sensor platforms 102a-102e may be communicated to the information service provider system 110 (e.g., via network 108 and/or the like). In certain embodiments, the information 106a-106e may be communicated directly to the information service provider system 110 from the sensors 104a-104e and/or the associated mobile sensor platforms 102a-102e. In other embodiments, the information 106a-106e may be communicated via one or more intermediate systems.

The information service provider system 110 may be configured to aggregate, manage, and/or otherwise operate on the received environmental information 106a-106e. In certain embodiments, the received information 106a-106e may be managed as part of an environmental information database 112 maintained by an environmental information management module 114 executing on the service provider system 110 configured to perform various database management activities in connection with the database 112. The environmental information database 112 may include, among other things, collected environmental information, identification information associated with sensors and/or mobile sensor platforms that collected the environmental information, geographic location information associated with the environmental information (e.g., information included in the environmental information obtained by a location-based sensor of an associated sensor platform), temporal information associated with the collected environmental information (e.g., a date and/or time indicating when the information was collected), and/or the like. In some embodiments, the environmental information management module 114 may use a mapping database 120 containing geographic information to generate a mapping and/or other association between the collected environmental information and geolocation data.

In some embodiments the user system 122 may be configured to interact with the information service provider system 110 in connection with performing a variety of operations. In certain embodiments, the user system 122 may issue requests 126 and/or receive associated responses 124 for information included in the environmental information database 112 managed by the service provider system 110, for data products derived from information included in the database 112, for the results of certain computations performed on information included in the database 112, and/or the like. In some embodiments, generation of responses 124 based on received requests 126 may be performed, at least in part, by the environmental information management module 114.

As an example, the user system 122 may issue a request 126 to the service provider system 110 for generation of one or more visualizations based on information included in the environmental information database 112. In response, the environmental information management module 114 may identify and access information in the information database 112 associated with the request 126, generate the one or more visualizations in accordance with the request based on the identified information, and send an associated response 124 including the visualizations to the user system 122. In further embodiments, the environmental information management module 114 may perform certain analytics on information included in the environmental information database 112 in response to received responses 126 and generate associated responses 124. It will be appreciated that the environmental information management module 114 may be configured to generate a wide variety of responses 126 based on information included in the information database 112 in accordance with received requests 124, and that any computational result and/or response generated using information included in the database 112 may be used in connection with the embodiments disclosed herein.

In some embodiments, information included in the environmental information database 112 may be associated with one or more defined policies and/or other rules that may be enforced by the environmental information management module 114 in connection with generating responses 126. Policies may, among other things, articulate how the environmental information may be used (e.g., used by the user system 122) and/or distributed from the environmental information service provider system 110 (e.g., distributed to other users and/or services). Such policies or rules can be articulated and implemented using any suitable mechanism including, for example, using the digital rights management techniques described in the '551 application and the '693 application. Exemplary policies that may be implemented by the systems and methods disclosed herein may include, without limitation, policies regarding what information may be collected by the environmental information service provider system 110 and how such information is collected (e.g., the conditions under which the information is collected, etc.), how the information may be used and/or distributed, limitations on collection of information (e.g., how many days of information should be collected, how long it should be retained, size limits on collected information, whether users can set/modify these limits, any/or any other desired limitations), and/or the like.

In certain embodiments, consistency and/or quality checking of information included in the environmental information database 112 may be performed by the information service provider system 110 and/or a module executing thereon (e.g., environmental information management module 114). For example, the environmental information service provider system 110 may compare a plurality of environmental information data points obtained by sensors 104a-104e of a plurality of mobile sensor platforms 102a-102e at a same and/or similar geographic location and/or time to identify outlier and/or potentially less accurate data points.

In some embodiments, the environmental information service provider system 110 may be further configured to score and/or otherwise attribute certain weights to data points, associated sensors 104a-104e, and/or associated mobile sensor platforms 102a-102e based on consistency and/or quality checking determinations. In certain embodiments, such scoring and/or weighting of environmental information data points, associated sensors 104a-104e, and/or mobile sensor platforms 102a-102e may be performed by a mobile sensor platform scoring engine 116 executing on the environmental information service provider system 110. A variety of scoring and/or weighting methodologies may be used in connection with the disclosed embodiments. For example, data points having relatively high consistency and/or correlation with other similar data points (e.g., proximately and/or temporally similar data points) may be attributed with a higher score and/or weight, whereas outlier data points may be attributed with a lower score and/or weight.

In one exemplary implementation utilizing the illustrated architecture, three mobile sensor platforms (i.e., sensor platforms "A", "B" and "C") may measure environmental information using associated sensors and provide the environmental information to the environmental information service provider system 110. The environmental information service provider system 110 may determine that the measured environmental information is of a same and/or similar type and/or was collected at a same and/or similar geographic location and/or time (e.g., based on comparisons with one or more thresholds).

An environmental information management module 114 and/or a mobile sensor platform scoring engine 116 executing on the environmental information service provider system 110 may compare the environmental information received from the three sensor platforms, and may determine that the information received from sensor platforms "A" and "B" are within a particular range (e.g., a predefined threshold range) but that the information received from sensor platforms "C" deviate from the range. Based on this consistency and/or quality checking determination, the mobile sensor platform scoring engine 116 may attribute a higher score and/or weight to the information received from sensor platforms "A" and "B" and/or to the sensor platforms themselves, while attributing a lower score and/or weight from the information received from sensor platform "C" and/or the sensor platform itself. In some embodiments, this lower score and/or weight may vary based on an extent the information received from sensor platform "C" deviates from the predetermined range.

In certain embodiments, scoring and/or weighting received environmental information, associated sensor platforms, and/or associated sensors may allow the environmental information service provider system 110 and/or users interacting with the same to prioritize use of higher scoring and/or weighted, and thus potentially more accurate, environmental information. For example, when two mobile sensor platforms have collected geographically and temporally similar information of a same and/or similar type, the environmental information service provider system 110 may compare scores associated with the information and/or sensor platforms and select the higher scoring and/or the information collected by a higher scoring sensor platform for use in connection with generating an associated response 124.

In certain embodiments, the environmental information service provider system 110 may expose certain information included in the environmental information database 112 for use in connection with issuing requests 126 to users (e.g., via user system 122 or the like). For example, in some embodiments, a mapping between geolocation information and information included in the environmental information database 112 may be provided to a user of a user system 122 (e.g., in response to the user selecting a particular geographic region of interest via an interface of the user system 122 and/or the like). The environmental service provider system 110 may further provide to a user of a user system 112 score and/or weight information for associated environmental information data points, sensors, and/or mobile sensor platforms. This information may be used by the user to provide an indication of a degree of trust and/or accuracy of the exposed data points, sensors, and/or sensor platforms. In some embodiments, the information exposed to a user of the user system 112 may hide and/or otherwise anonymize an individual and/or entity associated with the information and/or a collecting sensor and/or sensor platform, thereby preserving the privacy of individuals associated with the information and/or associated sensors and/or sensor platforms. In certain embodiments, this may be enforced via applied policies as discussed above.

As an example, a health organization may utilize a user system 122 to view available environmental information managed by the environmental information service provider system 110 for a particular geographic region of interest and a particular time of interest. Through interactions with the environmental information service provider system 110, the health organization may access pollen information, PM 2.5 information, and wind speed information for use in connection with generating a health forecast for individuals having respiratory issues.

In another example, a governmental transportation agency may wish to access measured noise and/or brightness information along a particular roadway to assess whether the roadway is a source of high noise levels and/or light pollution. Through interactions with the environmental information service provider system 110, the transportation agency may access measured noise and light information associated with geographic locations along the roadway of interest and use such information to identify areas where noise and/or light pollution mitigation techniques may be beneficial. In some embodiments, the transportation agency may be presented with scores and/or weights associated with accessed information, and may prioritize implementation of noise and/or light pollution mitigation in a particular geographic location based in part on relative scores and/or weights of information associated with the location.

In further embodiments, the environmental information service provider system 110 herein may facilitate user feedback relating to environmental information managed as part of the environmental information database 112. For example, in certain embodiments, if a user discovers an inconsistency between two temporally and geographically proximate data points differing by a significant amount, the user may communicate the inconsistency as feedback to the environmental information service provider system 110. The feedback may include, for example, an identification of the environmental information associated with the feedback, a geographic location associated with the environmental information, and/or a time associated with the environmental information.

Upon receipt of the feedback, the environmental service provider system 110 and/or a scoring engine 116 executing thereon may decrease a score and/or weight associated with the environmental information associated with the feedback. In further embodiments, the environmental service provider system 110 and/or a scoring engine 116 executing thereon may identify a mobile sensor platform and/or associated sensor that collected the information associated with the feedback and decrease a score and/or weight associated with the identified mobile sensor platform and/or sensor. In certain embodiments, prior to decreasing scores and/or weights associated with information, platforms, and/or sensors associated with feedback received from a first user, the environmental information service provider system 110 and/or scoring engine 116 may wait until feedback is received from a second user that corroborates the first user's feedback. In this manner, scores and/or weights may be decreased upon inconsistencies being identified by a plurality of users.

In an example involving the above-described governmental transportation agency, the agency may send individuals to visit a particular geographic location associated with high noise and/or light pollution identified based on information accessed from the environmental information database 112. Upon visiting the site, the individuals may determine that the noise and/or light pollution levels are not high and/or are not as high as indicated by the associated information accessed from the environmental information database 112. The individual and/or the transportation agency may notify the environmental information service provider system 110 of this discrepancy. In response, the environmental information may decrease a score and/or weight associated with the environmental information and/or the mobile sensor platform and/or associated sensor that collected the information.

In another example, a health organization may send individuals to visit a particular geographic location associated with high PM 2.5 pollution levels identified based on pollution information accessed from the environmental information database 112. Upon visiting the location, the individuals may determine that the PM 2.5 pollution levels are not high and/or are not as high as indicated by the associated information accessed from the environmental information database 112. The individuals and/or the health organization may notify the environmental information service provider system 110 of this discrepancy. In response, the environmental information service provider system 110 may decrease a score and/or weight associated with the environmental information and/or the mobile sensor platform and/or associated sensor that collected the information. In addition, as discussed in detail below, the environmental service provider system 110 may further incentivize and/or otherwise reward the individuals and/or health organization for reporting the discrepancy.

In some embodiments, users that provide feedback may be incentivized for providing corroborated feedback. For example, users that provide corroborated feedback and/or accounts associated with the same may be credited via monetary compensation and/or incentive points that may be redeemed and used to receive various products, services, and/or discounts. In some embodiments, the potential for users to collaborate with entities associated with mobile sensor platforms in connection with submitting inaccurate feedback may be reduced by not exposing uniquely identifying information associated with mobile sensor platforms when exposing environmental information collected by the platforms to a requesting user. In further embodiments, users that submit a certain threshold amount of feedback (e.g., a large amount of feedback) and/or frequently submits feedback that is not corroborated by other users may be identified by the environmental information service provider system 110 as suspicious, and future feedback from such a user may be disregarded and/or otherwise given less weight.

It will be appreciated that a number of variations can be made to the architecture, relationships, and examples presented in connection with FIG. 1 within the scope of the inventive body of work. For example, certain system functionalities described above (e.g., functionalities of systems 110, 122, mobile sensor platforms 102a-102e, and/or associated sensors 104a-104e) may be integrated into a single system and/or any suitable combination of systems in any suitable configuration. Thus it will be appreciated that the architecture, relationships, and examples presented in connection with FIG. 1 are provided for purposes of illustration and explanation, and not limitation.

Figure 2:
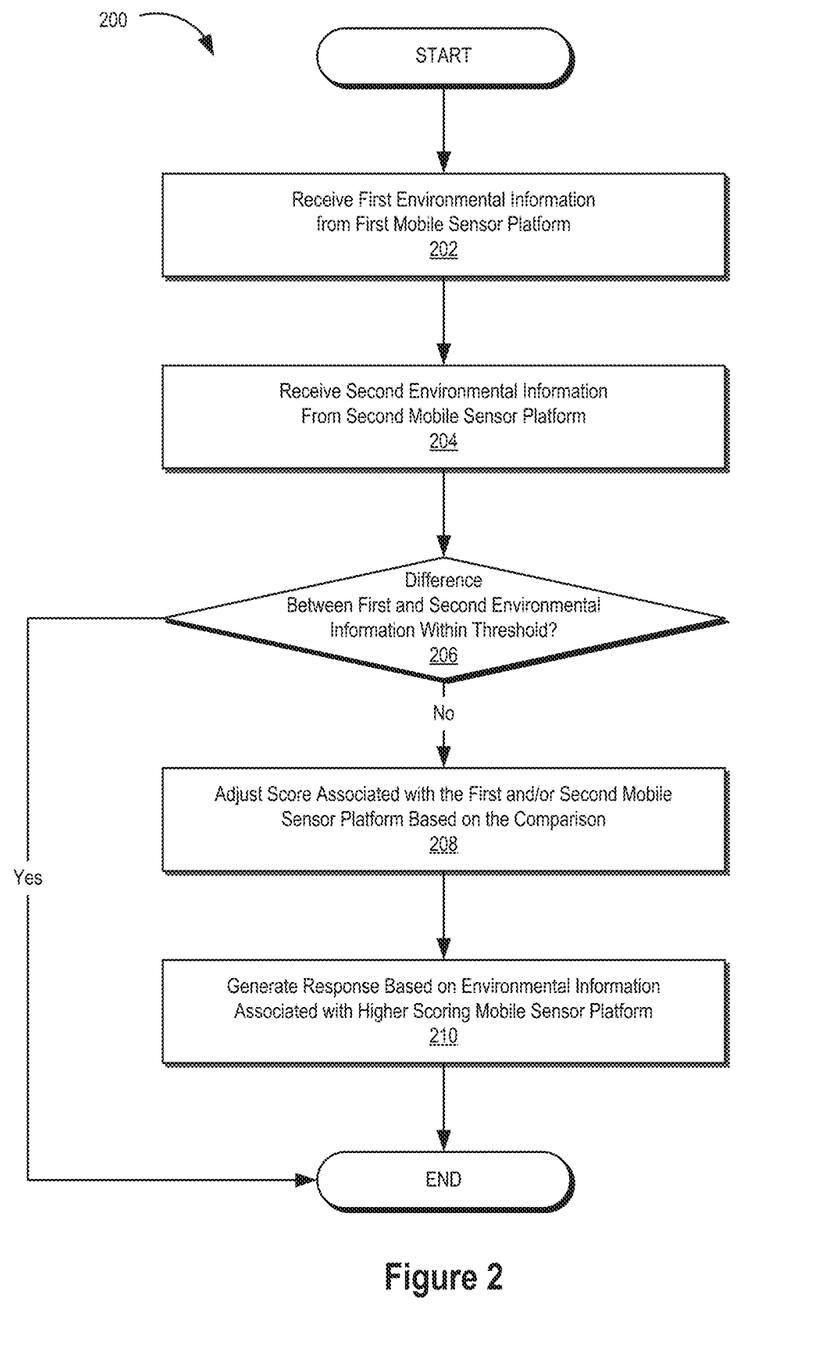
FIG. 2 illustrates a flow chart of an exemplary method of managing information from a plurality of mobile sensor platforms consistent with embodiments of the present disclosure.

FIG. 2 illustrates a flow chart of an exemplary method 200 of managing information from a plurality of mobile sensor platforms consistent with embodiments of the present disclosure. The illustrated method 200 may be implemented in a variety of ways, including using software, firmware, hardware, and/or any combination thereof. In certain embodiments, the method 200 and/or its constituent steps may be performed by an environmental service provider system, one or more user systems, one or more mobile sensor platforms and/or associated sensors, and/or any other suitable system or combination of systems. In certain embodiments, the illustrated method may facilitate consistency and/or quality checking of environmental information managed by an environmental information service provider and/or scoring and/or weighting of such information based on such determinations.

At 202, first environmental information may be received from a first mobile sensor platform. In certain embodiments, the first environmental information may be measured by a sensor associated with the first mobile sensor platform, and may comprise one or more of any of the types of environmental and/or other information described herein. The first environmental information may comprise, among other things, identification information associated with the first mobile sensor platform and/or an associated sensor, an indication of an associated type of environmental information, the measured and/or otherwise collected data points, an indication of a geographic location associated with the first environmental information, and an associated time (e.g., a measurement time associated with the first environmental information).

At 204, second environmental information may be received by a second mobile sensor platform. In certain embodiments, the second environmental information may be measured by a sensor associated with the second mobile sensor platform, and may comprise one or more of any of the types of environmental and/or other information described herein. Like the first environmental information, the second environmental information may comprise, among other things, identification information associated with the second mobile sensor platform and/or an associated sensor, an indication of an associated type of environmental information, the measured and/or otherwise collected data points, an indication of a geographic location associated with the second environmental information, and an associated time (e.g., a measurement time associated with the first environmental information).

A comparison may be performed at 206 based on the first environmental information and the second environmental information. In some embodiments, the comparison may determine whether the first environmental information and the second environmental information are associated with a same and/or similar geographic location (e.g., by determining that geographic information associated with data points of the first and second environmental information indicates that the data points are located within a certain threshold distance of each other using a mapping database or the like). The comparison may further determine whether the first and second environmental information are associated with a same and/or similar time (e.g., within a particular time period).

If the first environmental information is proximately and temporally similar to the second environmental information, the comparison at 206 may further include determining whether a difference between the data points associated with the first and second environmental information is within a particular threshold range that, in certain embodiments may comprise a predefined threshold range. For example, the first and second environmental information may comprise measured temperature information, and the comparison at 206 may determine whether the measured temperature information of the first and second environmental information are within 5% of each other. If the difference between the data points associated with the first and second environmental information is within the threshold range, the method 200 may proceed to terminate. If the difference between the data points associated with the first and second environmental information is outside the threshold range, the method 200 may proceed to 208.

At 208, a score and/or weight associated with the first and/or second environmental information included in an environmental information database may be adjusted based on the determination at 206. For example, if the first environmental information differs from the second environmental information by more than a threshold amount, and the second environmental information differs from other geographically and/or temporally same or similar environmental information included in the environmental information database by less than the threshold amount, it may be determined that the first environmental information comprises outlier information. Accordingly, at 208, a score and/or weight associated with the first environmental information may be reduced. In some embodiments, the score and/or weight may be reduced by an amount dependent on an amount the difference between the first and second environmental information exceeds the threshold.

In other examples, if the first environmental information differs from the second environmental information by more than a threshold amount, and the second environmental information also differs from other geographically and/or temporally same or similar environmental information included in the environmental information database by more than the threshold amount, it may be determined that both the first and second environmental information comprise outlier information. Accordingly, at 208, scores and/or weights associated with both the first and the second environmental information may be reduced (e.g., reduced based on an amount dependent on an amount the differences between the first, second and/or other environmental exceeds the threshold).

Upon receiving a request from a user system for a response generated based on environmental information associated with a same and/or similar geographic location and/or time associated with the first and second environmental information, a response may be generated at 210 based on the first and/or second environmental information according to a score and/or weight associated with the same. For example, if a score and/or weight associated with the first environmental information is higher than a score and/or weight associated with the second environmental information, the response may be generated based on the first environmental information. In further embodiments, if a score and/or weight associated with the first environmental information is higher than a score and/or weight associated with the second environmental information, the first environmental information may be weighted more heavily in generating the response than the second environmental information.

Figure 3:
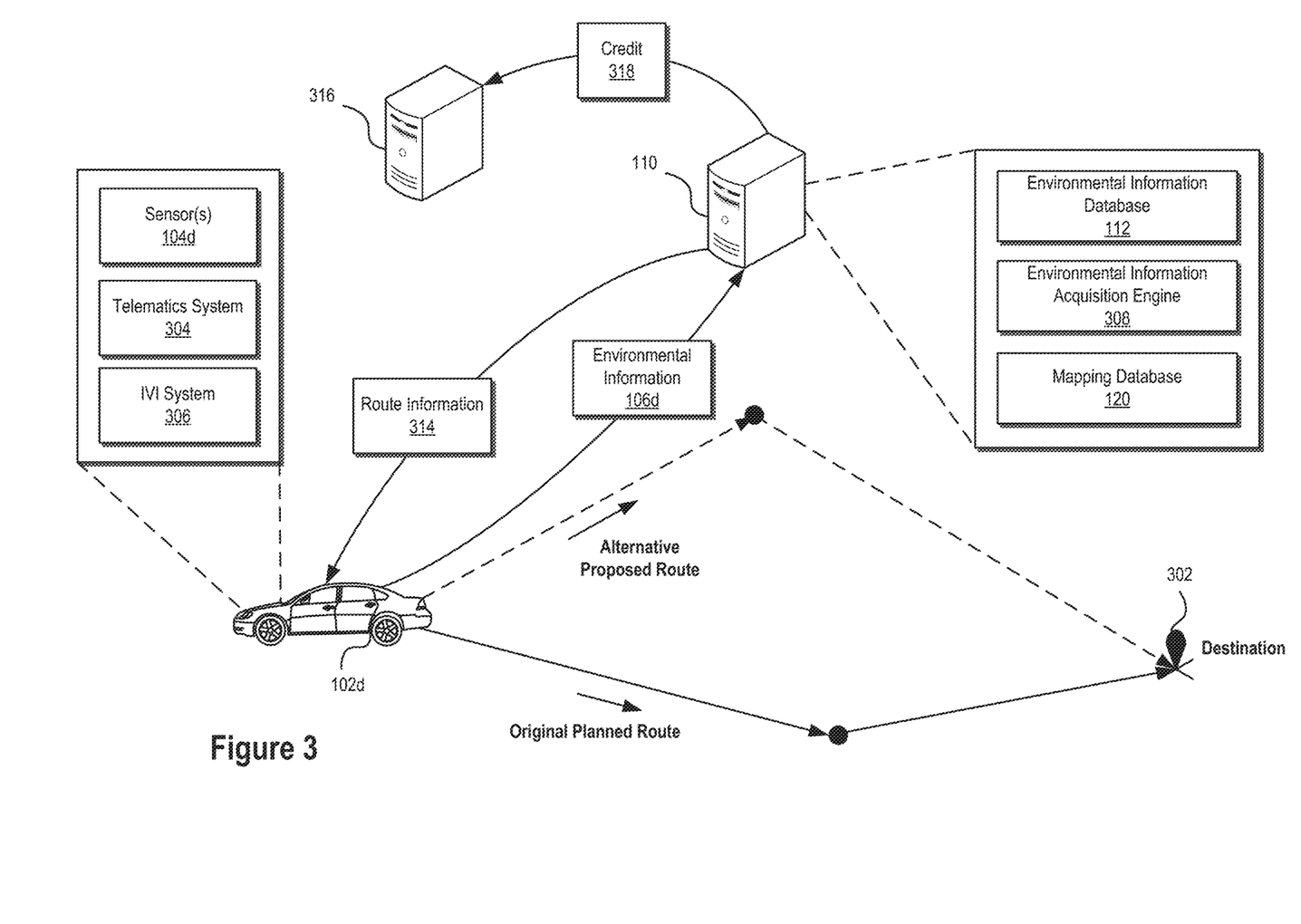
FIG. 3 illustrates information collection management by an information service provider system consistent with embodiments of the present disclosure.

FIG. 3 illustrates management of information collection by an information service provider system 110 consistent with embodiments of the present disclosure. Embodiments of the disclosed systems and methods may be used to incentivize and/or otherwise encourage the collection and/or acquisition of environmental information. For example, in certain circumstances, an environmental information service provider and/or an associated system 110 may wish to obtain environmental information associated with certain geographic areas, information collection times, and/or information types of interest. Such areas, times, and/or information types of interest may correspond to information areas, times, and/or information types that have not been previously collected by one or more mobile sensor platforms (e.g., mobile sensor platform 102*d*), information that has not been collected within a certain time period, and/or information or information that has been collected by a mobile sensor level attributed with less than a threshold score and/or weight.

To facilitate collection and/or acquisition of environmental information of interest, the environmental information service provider system 110 may utilize an environmental information acquisition engine 308 executing thereon. In some embodiments, the environmental information acquisition engine 308 may be configured to analyze information stored within the environmental information database 112 and/or the mapping database 120 to identify geographic areas, times, and/or information types of interest. Once environmental data of interest is identified, the environmental information acquisition engine 308 may identify one or more mobile sensor platforms 102*d* that may be capable of collecting and/or acquiring the environmental information of interest (e.g., based on the platform 102*d* being associated with a particular type of sensor 104*d*, an associated score and/or weight of the sensor platform 102*d*, and/or the like).

As an example, the environmental information acquisition engine 308 may identify that the environmental information database 112 does not include light pollution information for a particular geographic location. Similarly, the environmental information acquisition engine 308 may determine that light pollution information included in the environmental information database 112 is not associated with a sufficiently high score and/or weight, and therefore is potentially less reliable. Based on such identifications, the environmental information acquisition engine 308 may identify one or more mobile sensor platforms 102*d* and/or associated sensors 104*d* capable of collecting and/or otherwise acquiring such information. For example, the environmental information acquisition engine 308 may utilize information included in a database including information relating to available sensor platforms 102*d*, associated sensors 104*d* and/or geographic information relating to the same (e.g., real time geographic information obtained from a telematics system 304 included in the platform 102*d*, and/or a geographic region generally associated with the platform 102*d* and/or sensor 104*d* via a registration process or the like, etc.) to identify one or more mobile sensor platforms 102*d* and/or associated sensors 104*d* capable of collecting and/or otherwise acquiring environmental information of interest.

In further embodiments, one or more mobile sensor platforms 102*d* and/or associated sensors 104*d* capable of collecting and/or otherwise acquiring environmental information of interest may be identified based on an indication of an intended trip to a destination 302 by a user associated with the sensor platform 102*d*. For example, a driver of a sensor platform 102*d* comprising a vehicle may enter an intended destination 302 into a mapping and/or route finding interface of a telematics system 304 and/or an in-vehicle-infotainment system ("IVI") 306 associated with the vehicle. Information regarding the destination 302 and/or a planned route to the destination proposed by the mapping and/or route finding interface of the telematics 304 and/or IVI system 306 may be transmitted to the environmental information service provider system 110 from the mobile sensor platform 102*d*.

Based in part on the received destination and/or planned route information, the environmental information acquisition engine 308 may identify environmental information of interest that may be obtained by the mobile sensor platform 102*d* either along the planned route or along a different alternative route. If the environmental information of interest may be obtained by the mobile sensor platform 102*d* along a different route, the environmental information acquisition engine 308 may generate an associated proposed alternative route using information included within the environmental information database 112 and/or the mapping database 120. In other embodiments, the environmental information acquisition engine 308 may generate an associate alternative proposed travel time to facilitate acquisition of environmental information of interest at a particular time Associated route information 314 and/or travel time information may be sent to the mobile sensor platform 102*d* and/or a system associated with the same such as the telematics system 304 and/or the IVI system 306. A proposed alternative route and/or travel time may be displayed to the user based on the received route information 314 (e.g., via the telematics 304 and/or IVI system 306), thereby allowing the user to travel to the intended destination 302 via the alternative route and facilitating the collection of the environmental information of interest (e.g., environmental information 106*d*).

In some embodiments, the environmental information service provider system 110 and/or the environmental information acquisition engine 308 may incentivize one or more mobile sensor platforms 102*d* to obtain environmental information of interest. For example, in certain embodiments, users associated with a mobile sensor platform 102*d* may be provided monetary and/or incentive-based compensation for obtaining and/or otherwise acquiring environmental information of interest. As an example, a user may choose to travel along a proposed alternative route suggested by a telematics system 304 based on route information 314 transmitted from the environmental information service provider system 110. The user may provide an indication of such a route choice via the telematics system 304 and/or an IVI system 306 which may be transmitted to the environmental information service provider system 110. Based on receipt of this indication, the environmental information service provider system 110 may provide an indication 318 to an electronic currency management system 316 that an account associated with the user should be credited a certain amount in exchange for the user choosing to travel the route associated with the alternative route information 314. Such credits may comprise monetary compensation and/or incentive points that may be redeemed and used to receive various products, services, and/or discounts.

In other embodiments, an indication 318 may be sent by the environmental information service provider system 110 to the electronic currency management system 316 in response to a determination that the environmental information 106d of interest was received by the environmental information service provider system 110 from the mobile sensor platform 102d. In this manner, the indication 318 may be sent by the environmental information service provider system 110 based on the environmental information 106d of interest actually being collected by the mobile sensor platform 102d rather than based on an indication that a user associated with the platform 102d intends to collect the information. Using similar mechanisms, users that provide feedback relating to information included in the environmental information database 112 may be incentivized for providing corroborated feedback.

In an example using embodiments of the systems and methods facilitating collection of information by an information service provider system 110, a health organization may wish to obtain air pollution information for a particular geographic area at a particular time, but such information may not be available in the environmental information database 112. For example, pollution information may not have been previously collected for the particular area and/or collected during the time of interest, and thus may not be included in the environmental information database 112.

Using embodiments of the disclosed systems and methods, the health organization may offer various incentives to one or more mobile sensor platforms 102d, which may depend on scores and/or weights associated with the mobile sensor platforms 102d, for the collection of the air pollution information for the geographic area at the particular time. For example, the health organization may offer 10 credits for information obtained by a sensor platform 102d associated with a score of 90, 5 credits for information obtained by a sensor platform associated with a score of 50, and/or the like. Identified sensor platforms 102d may be sent proposed route information 314 by the environmental information service provider system 110 that facilitates the collection of the environmental information of interest (i.e., collection of air pollution information at the particular location and time). Upon receipt of the environmental information of interest 106d from one of the identified sensor platforms 102d, the environmental information service provider system 110 may transmit a corresponding credit to an account associated with a user associated with the sensor platform 102d.

Figure 4:
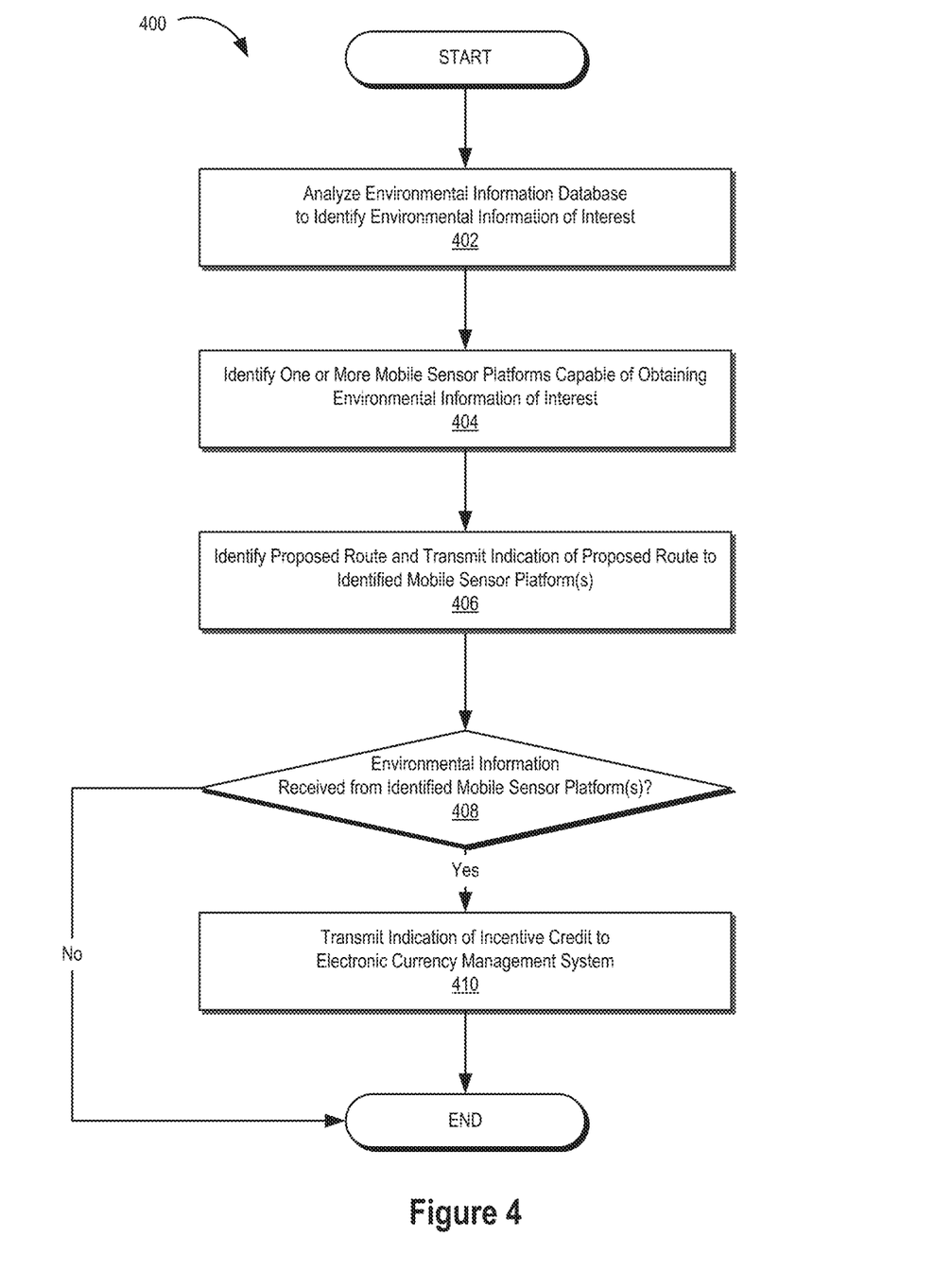
FIG. 4 illustrates a flow chart of an exemplary method of managing the collection of information by a mobile sensor platform consistent with embodiments of the present disclosure.

FIG. 4 illustrates a flow chart of an exemplary method 400 of managing the collection of information by a mobile sensor platform consistent with embodiments of the present disclosure. The illustrated method 400 may be implemented in a variety of ways, including using software, firmware, hardware, and/or any combination thereof. In certain embodiments, the method 400 and/or its constituent steps may be performed by an environmental service provider system, one or more user systems, one or more mobile sensor platforms and/or associated sensors, and/or any other suitable system or combination of systems. In certain embodiments, the illustrated method may facilitate collection and/or acquisition of environmental information of interest.

At 402, information included within an environmental information database and/or an associated mapping database may be analyzed to identify environmental information of interest. In certain embodiments, the environmental information of interest may comprise environmental information and/or environmental information associated with a threshold score and/or weight that is not included in the environmental information database. For example, in some embodiments, the environmental information of interest may be associated with certain geographic areas, information collection times, and/or information types of interest corresponding to information areas, times, and/or information types that have not been previously collected by one or more mobile sensor platforms, information that has not been collected within a certain time period (i.e., out of date information), and/or information that has been collected by a mobile sensor level associated with less than a threshold score and/or weight.

One or more mobile sensor platforms capable of obtaining the identified environmental information of interest may be identified at 404. In certain embodiments, the one or more mobile sensor platforms may be identified based on the platforms being geographically located proximate to an area associated with the environmental information of interest, by being associated with an environmental sensor capable of collecting the environmental information of interest, by being associated with a certain threshold score and/or weight, and/or by having provided an indication (e.g., via a telematics and/or IVI system or the like) of an intended destination proximate to and/or having a potential travel route proximate to an area associated with the environmental information or interest and/or at a particular time or within a particular time window, and/or the like.

At 406, a proposed route that facilitates the collection of the environmental information of interest by the one or more identified mobile sensor platforms may be identified (e.g., using information included in a mapping database and/or the like) and may be communicated to the one or more identified mobile sensor platforms. In certain embodiments, the proposed route may lead from a present location of the one or more mobile identified sensor platforms to a geographic area associated with the environmental information of interest as a final destination. In other embodiments, the proposed route may lead from a present location of the one or more identified sensor platforms to a geographic area associated with the environmental information of interest as an intermediate destination en route to a final destination.

A determination at 408 may identify whether the environmental information of interest has been received from the one or more identified mobile sensor platforms (e.g., received by the environmental information service provider and/or the like). If not, the method 400 may proceed to terminate. If so, the method 400 may proceed to 410.

At 410, to incentivize the collection and/or acquisition of environmental information of interest, an indication may be transmitted to an electronic currency management system 316 that an account associated with the user should be credited a certain amount in exchange for the collection and/or acquisition of the environmental information of interest. Such credits may comprise monetary compensation and/or incentive points that may be redeemed and used to receive various products, services, and/or discounts.

Figure 5:
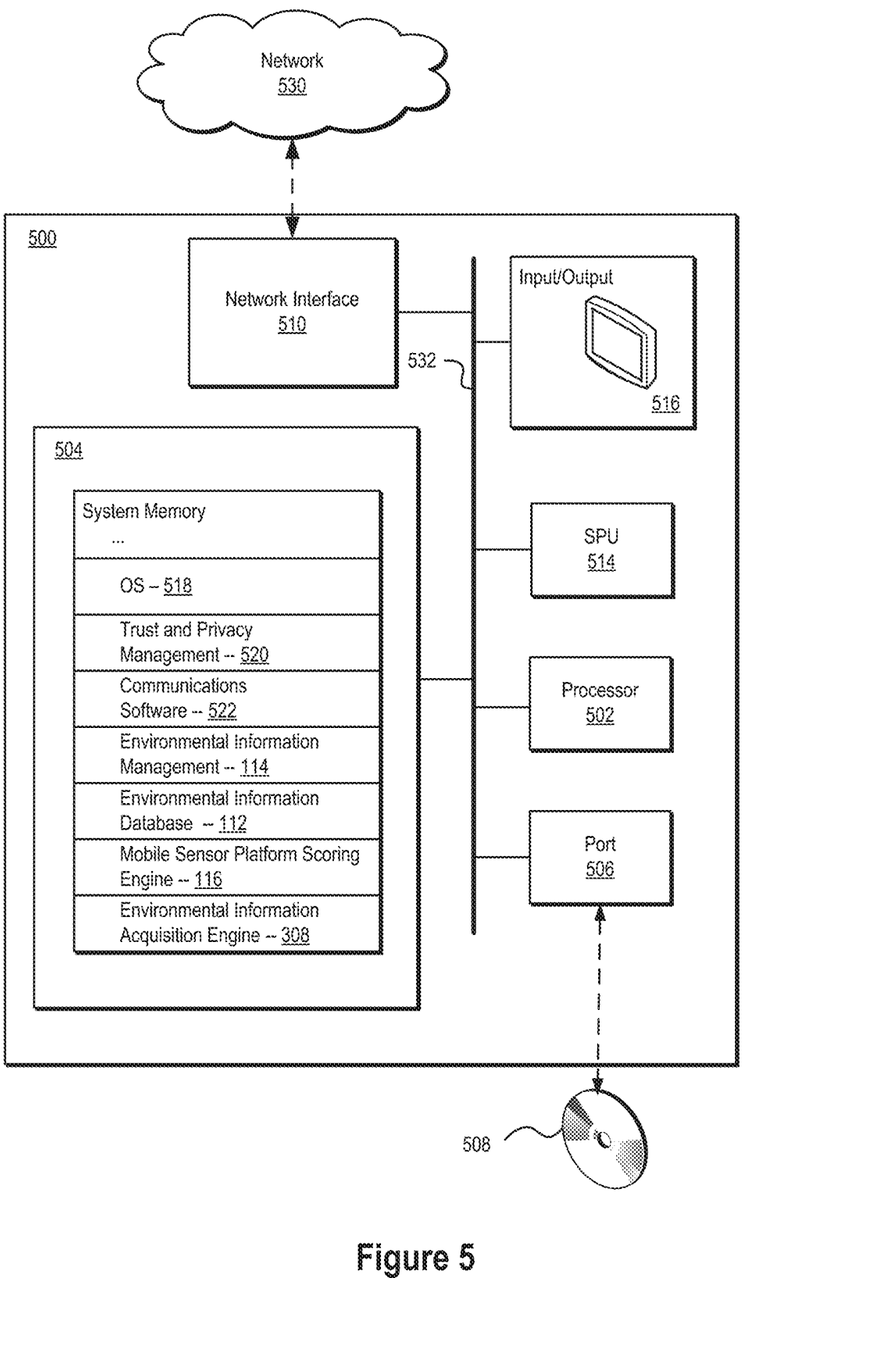
FIG. 5 illustrates an exemplary system that may be used to implement certain embodiments of the systems and methods disclosed herein.

FIG. 5 illustrates an exemplary system 500 that may be used to implement embodiments of the systems and methods disclosed herein. The exemplary system 500 may comprise a system and/or device associated with a user, an environmental information service provider system, a mobile sensor platform, an electronic currency management system, and/or any other system configured to implement embodiments of the systems and methods disclosed herein. As illustrated in FIG. 5, the system 500 may include: a processing unit 502; system memory 504, which may include high speed random access memory ("RAM"), non-volatile memory ("ROM"), and/or one or more bulk non-volatile non-transitory computer-readable storage mediums (e.g., a hard disk, flash memory, etc.) for storing programs and other data for use and execution by the processing unit 502; a port 506 for interfacing with removable memory 508 that may include one or more diskettes, optical storage mediums (e.g., flash memory, thumb drives, USB dongles, compact discs, DVDs, etc.) and/or other non-transitory computer-readable storage mediums; a network interface 510 for communicating with other systems via one or more network connections 530 using one or more communication technologies; a user interface 516 that may include a display and/or one or more input/output devices such as, for example, a touchscreen, a keyboard, a mouse, a track pad, and the like; and one or more busses 532 for communicatively coupling the elements of the system 500. In certain embodiments, the system 500 may include and/or be associated with one or more sensors (not shown) configured to collect various device data, including any of the types of sensors disclosed herein.

In some embodiments, the system 500 may, alternatively or in addition, include a SPU 514 that is protected from tampering by a user of system 800 or other entities by utilizing secure physical and/or virtual security techniques. An SPU 514 can help enhance the security of sensitive operations such as personal information management, trusted credential and/or key management, privacy and policy management, and other aspects of the systems and methods disclosed herein. In certain embodiments, the SPU 514 may operate in a logically secure processing domain and be configured to protect and operate on secret information, as described herein. In some embodiments, the SPU 514 may include internal memory storing executable instructions or programs configured to enable the SPU 514 to perform secure operations, as described herein.

The operation of the system 500 may be generally controlled by a processing unit 502 and/or a SPU 514 operating by executing software instructions and programs stored in the system memory 504 (and/or other computer-readable media, such as removable memory 508). The system memory 504 may store a variety of executable programs or modules for controlling the operation of the system 500. For example, the system memory 504 may include an operating system ("OS") 518 that may manage and coordinate, at least in part, system hardware resources and provide for common services for execution of various applications and a trust and privacy management system 520 for implementing trust and privacy management functionality including protection and/or management of personal data through management and/or enforcement of associated policies. The system memory 504 may further include, without limitation, communication software 522 configured to enable in part communication with and by the system 500, a mapping database (not shown), an environmental information management module 114, an environmental information database 112, a mobile sensor platform scoring engine 116, and environmental information acquisition engine 308, and/or any other information and/or applications configured to implement embodiments of the systems and methods disclosed herein.

The systems and methods disclosed herein are not inherently related to any particular computer, electronic control unit, or other apparatus and may be implemented by a suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers at one site or distributed across multiple sites and interconnected by a communication network. Software embodiments may be implemented as a computer program product that comprises a non-transitory storage medium configured to store computer programs and instructions, that when executed by a processor, are configured to cause the processor to perform a method according to the instructions. In certain embodiments, the non-transitory storage medium may take any form capable of storing processor-readable instructions on a non-transitory storage medium. A non-transitory storage medium may be embodied by a compact disk, digital-video disk, a magnetic tape, a Bernoulli drive, a magnetic disk, a punch card, flash memory, integrated circuits, or any other non-transitory digital processing apparatus memory device.

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not to be limited to the details given herein, but may be modified within the scope and equivalents of the appended claims.

What is claimed is:

1. A method performed by an information service provider system comprising a processor and a non-transitory computer-readable storage medium storing instructions that, when executed by the processor, cause the information service provider system to perform the method, the method comprising:
    receiving, at an interface of the information service provider system, an indication of an intended destination of a mobile sensor platform;
    identifying, based on the received indication of the intended destination of the mobile sensor platform and information included in an environmental information database managed by the information service provider system, a geographic area of interest, wherein identifying the geographic area of interest comprises:
        analyzing the information included in the environmental information database to identify desired environmental sensor data of interest to obtain, the desired environmental sensor data of interest being associated with the geographic area of interest, wherein identifying the desired environmental sensor data of interest comprises:
            analyzing the environmental information database to identify environmental sensor data that is not included in the environmental information database, and
            identifying the environmental sensor data that is not included in the environmental information database as the desired environmental sensor data of interest;
    identifying one or more proposed routes transiting, at least in part, the geographic area of interest, the one or more proposed routes having environmental sensor data to be collected by the information service provider system;
    generating, using mapping information included in a mapping database, proposed route information for the mobile sensor platform, the proposed route information being associated with at least one of the one or more proposed routes; and transmitting, from the interface of the information service provider system to a system associated with the mobile sensor platform, the proposed route information.

2. The method of claim 1, wherein the indication of the intended destination of the mobile sensor platform is received from the mobile sensor platform.

3. The method of claim 1, wherein the indication of the intended destination of the mobile sensor platform is received from a telematics system associated with the mobile sensor platform.

4. The method of claim 1, wherein the indication of the intended destination of the mobile sensor platform comprises an intended route of the mobile sensor platform.

5. The method of claim 4, wherein the proposed route information is different, at least in part, than the intended route of the mobile sensor platform.

6. The method of claim 1, wherein identifying the geographic area of interest further comprises determining, based on the received indication of the intended destination of the mobile sensor platform, that a planned route to the intended destination of the mobile sensor platform is within a threshold distance to the geographic area of interest.

7. The method of claim 1, wherein the desired environmental sensor data of interest comprises data associated with a particular time period not included in the environmental information database managed by the information service provider system.

8. The method of claim 1, wherein the desired environmental sensor data of interest comprises a type of data not included in the environmental information database managed by the information service provider system.

9. The method of claim 1, wherein the method further comprises determining a score associated with the mobile sensor platform.

10. The method of claim 9, wherein the desired environmental sensor data of interest comprises sensor data associated with a score at or below the score associated with the mobile sensor platform.

11. The method of claim 1, wherein the mobile sensor platform comprises at least one environmental sensor.

12. The method of claim 1, wherein the at least one environmental sensor comprises at least one of a pollen level information sensor, an air particulate information sensor, a wind speed information sensor, a wind direction information sensor, a temperature information sensor, a humidity information sensor, a noise level information sensor, a light level information sensor, and an ozone level information sensor.

13. The method of claim 1, wherein the mobile sensor platform comprises at least one of a passenger vehicle, a transit vehicle, a train, a train car, a bicycle, a wearable electronic device, and a portable electronic device.

* * * * *